US00PP24841P2

(12) United States Plant Patent
Wood

(10) Patent No.: US PP24,841 P2
(45) Date of Patent: Sep. 2, 2014

(54) BARBERRY PLANT NAMED 'MIMI'

(50) Latin Name: *Berberis thunbergii*
Varietal Denomination: Mimi

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 173 days.

(21) Appl. No.: 13/507,786

(22) Filed: Jul. 27, 2012

(51) Int. Cl.
*A01H 5/00* (2006.01)

(52) U.S. Cl.
USPC ..... Plt./241

(58) Field of Classification Search
CPC ..... A01H 5/12
USPC ..... Plt./241
See application file for complete search history.

*Primary Examiner* — June Hwu
(74) *Attorney, Agent, or Firm* — C. A. Whealy

(57) ABSTRACT

A new and distinct cultivar of Barberry plant named 'Mimi', characterized by its compact and low mounding plant habit; vigorous growth habit; freely branching habit; leaves that are dark purple in color; good garden performance; and resistance to Black Stem Rust.

1 Drawing Sheet

Botanical designation: *Berberis thunbergii.*
Cultivar denomination: 'MIMI'.

BACKGROUND OF THE INVENTION

The present invention relates to a new and distinct cultivar of Barberry plant, botanically known as *Berberis thunbergii* and hereinafter referred to by the name 'Mimi'.

The new Barberry plant is a product of a planned breeding program conducted by the Inventor in Grand Haven, Mich. The objective of the breeding program was to develop new unique Barberry plants with attractive foliage, improved stress tolerance and resistance to Black Stem Rust (*Puccinia graminis*).

The new Barberry plant originated from an open-pollination in June, 2003 of Barberry *thunbergii* 'Concorde', not patented, as the female, or seed parent and an unknown selection of Barberry *thunbergii* as the male, or pollen, parent. The new Barberry plant was discovered and selected by the Inventor during the summer of 2006 as a single plant within the progeny of the stated open-pollination in a controlled environment in Grand Haven, Mich.

Asexual reproduction of the new Barberry plant by softwood cuttings in a controlled greenhouse environment in Grand Haven, Mich. since the summer of 2007 has shown that the unique features of this new Barberry plant are stable and reproduced true to type in successive generations of asexual reproduction.

SUMMARY OF THE INVENTION

Plants of the new Barberry have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Mimi'. These characteristics in combination distinguish 'Mimi' as a new and distinct Barberry plant:

1. Compact and low mounding plant habit.
2. Vigorous growth habit.
3. Freely branching habit.
4. Leaves that are dark purple in color.
5. Good garden performance.
6. Resistance to Black Stem Rust.

Plants of the new Barberry can be compared to plants of the female parent, 'Concorde'. Plants of the new Barberry differ from plants of 'Concorde' in the following characteristics:

1. Plants of the new Barberry are more vigorous than plants of 'Concorde'.
2. Plants of the new Barberry and 'Concorde' differ in leaf color as plants of 'Concorde' have dark purple red-colored leaves.

Plants of the new Barberry can be compared to plants of the *Berberis thunbergii* 'Crimson Pygmy', not patented. In side-by-side comparisons conducted in Grand Haven, Mich., plants of the new Barberry differed from plants of 'Crimson Pygmy' in the following characteristics:

1. Plants of the new Barberry grew more uniformly than plants of 'Crimson Pygmy'.
2. Plants of the new Barberry were more compact than plants of 'Crimson Pygmy'.
3. Plants of the new Barberry were more freely branching than plants of 'Crimson Pygmy'.

Plants of the new Barberry can be also compared to plants of the *Berberis thunbergii* 'Bagatelle', not patented. In side-by-side comparisons conducted in Grand Haven, Mich., plants of the new Barberry differed from plants of 'Bagatelle' in the following characteristics:

1. Plants of the new Barberry were more vigorous than plants of 'Bagatelle'.
2. Plants of the new Barberry and 'Bagatelle' differed in leaf color as plants of 'Bagatelle' had brownish burgundy-colored leaves.

BRIEF DESCRIPTION OF THE PHOTOGRAPH

The accompanying colored photograph illustrates the overall appearance of the new Barberry plant showing the colors as true as it is reasonably possible to obtain in colored reproductions of this type. Colors in the photograph may differ slightly from the color values cited in the detailed botanical description which accurately describe the colors of the new Barberry plant.

The photograph is a side perspective view of a typical plant of 'Mimi' grown in an outdoor nursery.

DETAILED BOTANICAL DESCRIPTION

The aforementioned photograph and following observations, measurements and values describe plants grown during the spring and summer in an outdoor nursery in Grand Haven, Mich. and under cultural practices which closely approximate commercial production. Plants used for the photograph and description were two years old. In the following detailed description, color references are made to The Royal Horticultural Society Colour Chart, 1995 Edition, except where general terms of ordinary dictionary significance are used.

Botanical classification: *Berberis thunbergii* 'Mimi'.

Parentage:

*Female, or seed, parent.*—Barberry *thunbergii* 'Concorde', not patented.

*Male, or pollen, parent.*—Unknown selection of Barberry *thunbergii*, not patented.

Propagation:

*Type.*—By softwood cuttings.

*Time to initiate roots, summer.*—About 70 days at 20° C.

*Time to produce a rooted young plant, summer.*—About one year at 20° C.

*Root description.*—Fine to medium; somewhat fleshy and fibrous; yellow in color.

*Rooting habit.*—Freely branching; dense.

Plant description:

*Plant form and growth habit.*—Perennial shrub; compact and low mounding plant habit; slow growth rate and vigorous growth habit; freely branching habit with about 89 lateral branches developing per plant.

*Plant height.*—About 22 cm.

*Plant diameter (area of spread).*—About 50 cm.

Lateral branch description:

*Length.*—About 13 cm.

*Diameter.*—About 2.5 mm.

*Internode length.*—About 1 cm.

*Aspect.*—Erect to outwardly spreading.

*Strength.*—Strong, flexible.

*Texture.*—Smooth, glabrous.

*Color.*—Close to 202A.

*Thorns.*—Quantity: About one thorn develops at each node. Length: About 1 cm. Width: About 0.75 mm. Color: Close to 202A.

Foliage description:

*Arrangement.*—Alternate or whorled; simple.

*Length.*—About 1.9 cm.

*Width.*—About 9 mm.

*Shape.*—Roughly spatulate.

*Apex.*—Mucronate.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 187A. Developing leaves, lower surface: Between 181A and 178A. Fully expanded leaves, upper surface: Close to 187A; venation, close to 187A; plants maintain dark purple coloration during the autumn. Fully expanded leaves, lower surface: Close to 178A; venation, close to 178A.

*Petiole.*—Length: About 6 mm. Diameter: About 3 mm. Texture, upper and lower surfaces: Smooth, glabrous. Color, upper and lower surfaces: Close to 187A.

Flower description:

*Flower arrangement and habit.*—Flowers arranged in terminal umbellate fascicles of one to three flowers; flowers face outwardly to drooping; freely flowering habit with about 49 flowers per plant.

*Fragrance.*—None detected.

*Natural flowering season.*—Plants of the new Barberry flower during the month of May in Grand Haven, Mich.

*Flower longevity.*—Flowers last about two weeks on the plant; flowers not persistent.

*Flower diameter.*—About 9 mm.

*Flower length (height).*—About 5 mm.

*Flower buds.*—Length: About 3 mm to 4 mm. Diameter: About 3 mm to 4 mm. Shape: Rounded, globose. Color: Close to 187A.

*Petals.*—Arrangement: Five to six petals in a single whorl. Length: About 4 mm. Width: About 3 cm. Shape: Elliptic. Apex: Obtuse. Margin: Entire. Texture, upper and lower surfaces: Smooth, glabrous. Color: When opening, upper surface: Close to 12C tinted with close to 46A to 46B. When opening, lower surface: Close to 12B to 12C. Fully opened, upper and lower surfaces: Close to 12B to 12C; color becoming closer to 12D with development.

*Sepals.*—Arrangement: Six sepals in a single whorl. Length: About 4 mm. Width: About 3 mm. Shape: Roughly orbicular. Apex: Acute to obtuse. Base: Acute to obtuse. Margin: Entire. Texture, upper and lower surfaces: Smooth; glabrous. Color: When developing, upper surface: Close to 12C. When developing, lower surface: Close to 46A to 46B. Fully developed, upper surface: Close to 12C. Fully developed, lower surface: Close to 12C tinted with close to 46A to 46B.

*Peduncles.*—Length: About 6 mm. Diameter: About 1 mm. Aspect: Erect to about 45° from vertical. Strength: Strong; flexible. Texture: Smooth, glabrous. Color: Close to 146B.

*Reproductive organs.*—Stamens: Quantity: Six per flower. Anther shape: Globular. Anther length: About 1 mm. Anther color: Close to 12A. Pollen amount: Scarce. Pollen color: Close to 12A. Pistils: Quantity: One per flower. Pistil length: About 3.5 mm. Style length: About 3 mm. Style color: Close to 137B. Stigma color: Close to 157B. Ovary color: Close to 137B. Seeds and fruits: Seed and fruit development have not been observed on plants of the new Barberry.

Garden performance: Plants of the new Barberry have been observed to have excellent garden performance and to tolerate rain, wind and temperatures ranging from about −30° C. to about 32° C.

Pathogen & pest resistance: Plants of the new Barberry have been observed to be resistant to Black Stem Rust (*Puccinia graminis*). Plants of the new Barberry have not been shown to be resistant to pests and other pathogens common to Barberry plants.

It is claimed:

1. A new and distinct Barberry plant named 'Mimi' as illustrated and described.

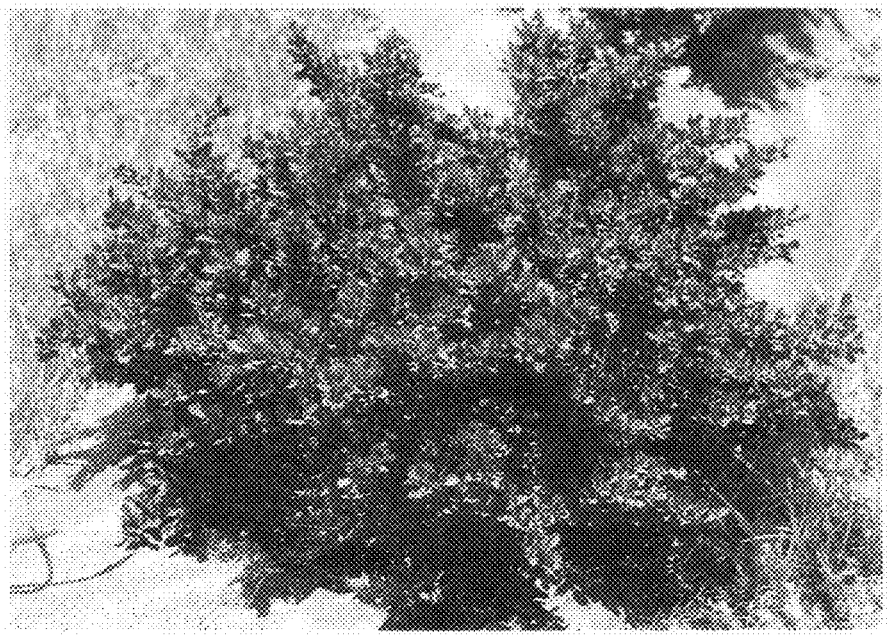

* * * * *